US005236840A

United States Patent [19]
Loh et al.

[11] Patent Number: 5,236,840
[45] Date of Patent: Aug. 17, 1993

[54] METHOD FOR GROWING CRUSTACEAN VIRUS IN FISH CELLS

[75] Inventors: Philip C. Loh; Yuanan Lu, both of Honolulu, Hi.

[73] Assignee: University of Hawaii, Honolulu, Hi.

[21] Appl. No.: 466,895

[22] Filed: Jan. 18, 1990

[51] Int. Cl.$^5$ .......................... C12N 7/00; C12N 7/02
[52] U.S. Cl. .................... 435/235.1; 435/239
[58] Field of Search .............................. 435/235.1, 239

[56] References Cited

U.S. PATENT DOCUMENTS

| | | | |
|---|---|---|---|
| 4,009,259 | 2/1977 | Ament et al. | 424/89 |
| 4,112,946 | 9/1978 | Herschler | 128/253 |
| 4,333,922 | 6/1982 | Herschler | 424/89 |
| 4,522,809 | 6/1985 | Adamowicz et al. | 424/89 |
| 4,687,744 | 8/1987 | Kerwin et al. | 435/242 |

OTHER PUBLICATIONS

Lu et al. *Journal of Virological Methods.* vol. 26 1989. pp. 339-344.

*Primary Examiner*—Douglas W. Robinson
*Assistant Examiner*—L. Blaine Lankford
*Attorney, Agent, or Firm*—Heller, Ehrman, White & McAuliffe

[57] ABSTRACT

A method is provided, whereby a crustacean virus is grown in fish cells. In particular, infectious hypodermal and hematopoietic necrosis virus (IHHNV) is grown in the established fish cell line, epithelioma papillosum cyprini (EPC).

12 Claims, No Drawings

METHOD FOR GROWING CRUSTACEAN VIRUS IN FISH CELLS

BACKGROUND OF THE INVENTION

The infectious hypodermal and hematopoietic necrosis virus (IHHNV) is an economically significant pathogen of penaeid shrimp grown in mariculture. The virus has a broad host species range; it may kill up to 90% of the juveniles of certain penaeid shrimp species.

The penaeid shrimp virus IHHNV has been isolated from infected shrimps. ( Y. N. Lu, P. C. Loh, and J. A. Brock, "Isolation and Characterization of the Infectious Hypodermal and Hematopoietic Necrosis Virus of penaeid Shrimp," 89th Annual Meeting, American Society for Microbiology, New Orleans, La., May 14–18, 1989.) The virus has been found to have a buoyant density in CsCl of 1.33 g/cm$^3$. Electron microscopical studies have shown the virus to exist as isometric particles with a size of 19±1 nm. Also, colorimetric analyses of the viral nucleic acid by the orcinol test have shown that the virus contains RNA. (Shatkin, A. J. in "Fundamental Techniques in Virology", Habel, K. and Salzman, N. P., eds. p. 23, Academic Press, N.Y. (1969)).

Previously, biological and biochemical studies of IHHNV have been limited because the virus could only be grown in young post-larval shrimps using an indicator shrimp bioassay. (Lightner et al., *J. World Maric. Soc.* 14:212–225, 1983). Consequently, the lack of an in vitro cell culture method for IHHNV made it difficult to develop serologically based methods useful for the rapid detection of the virus in shrimp stocks. Additionally, the only available method of IHHNV assay formerly available, the in vivo indicator shrimp bioassay procedure, is expensive, time consuming (on the order of days to weeks), and requires highly trained personnel.

The growth of crustacean virus according to the present invention provides a readily available source of cultured virus useful for development of immune sera for the rapid detection of virus in its habitat.

DESCRIPTION OF THE INVENTION

In brief, the present invention provides for an in vitro method of growth of crustacean virus in a fish cell line. In a preferred embodiment, the penaeid shrimp virus IHHNV is grown in an established culture of epithelioma papillosum cyprini (EPC), a cell line derived from proliferative skin lesions of carp, *Cyprinus carpio*. Initially, the host culture containing the fish cell line may be grown, typically at around 20° C., as a monolayer on a solid surface in a suitable nutrient medium, such as Eagle's minimal essential medium (MEM) supplemented with 10% fetal bovine serum (10FBS). If the IHHNV is used it is added to the culture and typically is adsorbed to host cells, such as EPC cells, at room temperature for one hour. A suitable growth medium will typically be added and the cells will be incubated at about 20° to 25°C. The culture may be monitored by light microscopy to assess cytopathology secondary to IHHNV infection. The virus will typically complete exponential growth within 48 hours. The virus is then harvested, preferably by suspension of the culture in phosphate-buffered saline (pH about 7.5), freezing-thawing, centrifugation; collection of the supernatant, extraction with trifluro-trichloroethane, and precipitation in the aqueous phase with PEG-NaCl. Upon purification, virus yields may be attained at $10^8$TCID$_{50}$/ml or higher.

Virus which has been adapted as described above in EPC cells, may be further cultured in other fish cells lines such cells from grass carp (GC), using the culturing method described herein.

The culturing of IHHNV using EPC cells under a solid overlay also provides a plaque quantitative assay of the titer of IHHNV. By this method, a count of the foci of lesions caused by the virus can be quantitatively correlated with cultures of known quantities of virus.

It will be appreciated that various modifications of the above description may be made without departing from the scope of the invention. The following examples are provided by way of illustration and are not intended to limit the invention in any way.

EXAMPLE 1

The starting monolayer cultures of EPC are grown on Eagle's minimal essential medium (MEM) supplemented with 10% fetal bovine serum (10FBS), at 20° C., using plastic tissue containers of culture grade. The IHHNV used for inoculation of the EPC cells in the present invention was obtained from IHHNV-infected shrimp as described by Lu, supra. The IHHNV was then banded in cesium chloride (CsCl). The EPC monolayer was then infected with ten-fold dilutions of the CsCl-banded IHHNV. Viral adsorption to the cells is accomplished by retaining the cells together with the virus at room temperature for one hour. Thereafter, experimental medium, MEM10FBS, is added and the infected culture is re-incubated at 20°C.

During development the cell cultures were examined daily by light microscopy. Using light microscopy it was possible to detect focal areas of cytopathology, following application of undiluted virus, as early as two days following infection. The foci of cytopathology progressively increased in size. The counting of these foci may be used as a quantitative assay of viral concentration (or yield) when correlated to the number of such foci in known samples treated under identical conditions. By the fifth day post-infection almost the entire monolayer was destroyed. Where the cultures were infected with higher virus dilutions, cytopathology was not evident until later. Infectivity titres, as estimated by the 50% tissue culture infectious dose end point (TCID$_{50}$) were $10^6$TCID$_{50}$/ml, using the method of Reed et al., *Amer. J. Hyg.* 27, 493–497 (1938).

Virus was harvested from the infected cultures and was serially passaged five times in EPC cells. As a general harvesting procedure, after collection of the virus-producing plaques, a 33% homogenized suspension in phosphate-buffered saline (PBS), pH 7.5, was prepared and the homogenate frozen and thawed three times. After slow speed centrifuge (1000 rpm, 10 min., 4°C.), the supernatant was collected and treated with trifluorotrichloroethane (Genetron 113) and the aqueous supernatant precipitated with polyethylene glycol-NaCl mixture (8% PEG in 0.125 M NaCl). The precipitate was recovered by slow speed centrifugation and resuspended in PBS. After centrifugation at 10,000 rpm, 20 minutes, 4° C., the recovered supernatant was centrifuged at 40,000 rpm., 1.5 hours at 4°C, and the pellet resuspended in PBS. For final purification the virus was isopycnically banded in CsCl and fractions were collected from the bottom of the tube and optical densities at 260 nm and 280 nm, respectively, read. Virus yields were as high as $10^8$TCID$_{50}$/ml. Isopycnic ultracentrifugation in CsCl of such passaged virus preparations yielded particles with a buoyant density of 1.33g/cm$^3$, similar to that of the original virus isolates. When the passaged virus preparations were negatively stained with 2% phosphotungstic acid and then examined by electron microscopy, only naked isometric particles of 19±1 nm diameter were seen. This particle size also corresponded to that of the original virus isolates.

The one-step growth cycle of the virus in EPC cells showed an eclipse period of about 3 hours, which was followed by an exponential growth phase which was completed by 48 hours post-infection. The virus yield at 48 hours post-infection was $10^{8.3}$TCID$_{50}$/ml.

EXAMPLE 2

Colorimetric analyses by the orcinol procedure of the starting IHHNV isolates revealed that the IHHNV contained RNA. That the virus contained RNA was reaffirmed using 5-bromo-2-deoxyuridine (BUDR), a DNA antagonist. At a concentration of 20ug/ml BUDR did not inhibit the replication of IHHNV in the EPC cells. In contrast, BUDR did interfere with the replication of DNA-containing vaccinia virus. Similarly, an inhibitory result was obtained when BUDR was used on the DNA-containing fish virus, channel catfish virus. An inhibitory result did not occur when BUDR was used to treat the RNA-containing fish virus, spring viremia of carp virus.

What is claimed is:

1. A method for growing crustacean virus comprising the steps of:
   introducing IHHNV virus particles into an established cell culture comprising epithelioma papillosum cyprini, derived from *Cyprinus carpio*;
   incubating said culture in a nutrient medium suitable for growth and replication of said virus; and
   harvesting said virus from said culture.

2. A method according to claim 1 wherein said nutrient medium comprises minimal essential medium supplemented with fetal bovine serum.

3. A method according to claim 1 wherein said culture is incubated at about 20°C.

4. A method according to claim 1 wherein said virus harvested from said culture is characterized by a buoyant density of about 1.33g/cm$^3$ in CsCl.

5. A method according to claim 1 wherein said virus harvested from said culture is characterized by isometric particles of an average size of 19±1 nm.

6. The method according to claim 1 wherein said harvesting comprises the steps of:
   (a) forming a homogenate containing said virus in a buffered saline solution at a pH of about 7.5;
   (b) freezing and thawing said homogenate;
   (c) centrifuging said homogenate and collecting the supernatant;
   (d) extracting said supernatant with trifluorotrichloroethane and collecting the aqueous phase;
   (e) adding a polyethylene-glycol-NaCl mixture to said aqueous phase to form a virus-containing precipitate;
   (f) recovering said precipitate by centrifugation;
   (g) purifying said precipitate by resuspension in buffered saline and by centrifugation;
   (h) further purifying said precipitate by isopycnically separation.

7. A method according to claim 6 wherein said buffered saline is phosphate buffered.

8. A method according to claim 6 wherein in said step (b), the freezing and thawing is performed three times.

9. A method according to claim 6 wherein in said step (c), centrifuging is at about 1000 rpm for about 10 minutes at about 4°C.

10. A method according to claim 6 wherein in said step (e) said mixture comprises about 8% by weight polyethylene-glycol in about 0.125 M NaCl.

11. A method according to claim 6 wherein said step (g) comprises resuspending said precipitate in phosphate buffered solution, centrifuging at about 10,000 rpm for about 20 minutes at about 4°C., and separating and centrifuging the supernatant formed thereby at about 40,000 rpm for about 1.5 hr. at about 4°C., then recovering the pelletized precipitate formed thereby.

12. A method according to claim 6 wherein said step (h) comprises resuspending said precipitate in phosphate buffer solution, iscopycrically banding said solution in CsCl and collecting the virus-containing fractions.

* * * * *

UNITED STATES PATENT AND TRADEMARK OFFICE
CERTIFICATE OF CORRECTION

PATENT NO. : 5,236,840
DATED : August 17, 1993
INVENTOR(S) : Philip C. Loh, et al It is certified that error appears in the above-indentified patent and that said Letters Patent is hereby corrected as shown below:

Column 4, line 22, "isopycnically" should be
--isopycnic--

Column 4, line 43, "isopycrically" should be
--isopycnically--

Signed and Sealed this

Twenty-ninth Day of March, 1994

Attest:

BRUCE LEHMAN

*Attesting Officer*  *Commissioner of Patents and Trademarks*